US008816136B2

(12) United States Patent
Kitamura et al.

(10) Patent No.: US 8,816,136 B2
(45) Date of Patent: Aug. 26, 2014

(54) METHOD FOR PRODUCING ALICYCLIC ALCOHOL

(75) Inventors: Mitsuharu Kitamura, Okayama (JP); Shinji Kotachi, Wakayama (JP); Shinya Nagasawa, Wakayama (JP); Yoshiharu Ataka, Wakayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 306 days.

(21) Appl. No.: 13/381,504

(22) PCT Filed: Jun. 30, 2010

(86) PCT No.: PCT/JP2010/061217
§ 371 (c)(1),
(2), (4) Date: Jun. 5, 2012

(87) PCT Pub. No.: WO2011/002044
PCT Pub. Date: Jun. 1, 2011

(65) Prior Publication Data
US 2012/0238784 A1    Sep. 20, 2012

(30) Foreign Application Priority Data
Jul. 1, 2009 (JP) .................................. 2009-157125

(51) Int. Cl.
*C07C 31/13* (2006.01)
(52) U.S. Cl.
USPC ............ 568/831; 568/835; 568/874; 568/875
(58) Field of Classification Search
USPC ................... 568/831, 835, 874, 875
See application file for complete search history.

(56) References Cited

U.S. PATENT DOCUMENTS

| 2,501,200 A * | 3/1950 | Wearn ........................... 568/444 |
| 5,463,095 A | 10/1995 | Shiokawa et al. |
| 6,919,489 B1 * | 7/2005 | McCusker-Orth ............ 568/864 |
| 7,432,390 B2 | 10/2008 | Kitamura et al. |

FOREIGN PATENT DOCUMENTS

| JP | 6-345688 | 12/1994 |
| JP | 9-328451 | 12/1997 |
| JP | 2006-282658 | * 10/2006 ............. C07C 51/47 |
| JP | 2009-149577 | 7/2009 |

OTHER PUBLICATIONS

International Search Report issued on Sep. 7, 2010 in PCT/JP10/061217 filed on Jun. 30, 2010.
Office Action Issued Dec. 12, 2013 in Chinese Patent Application No. 201080037796.8, filed Jun. 30, 2010.
"Carbonylation of terpenes", S.D. Pirozhkov et al., Bulletin of the Academy of Sciences of the USSR, Division of chemical science, vol. 28, Issue 4, pp. 784-790, 1979.

* cited by examiner

*Primary Examiner* — Sudhakar Katakam
*Assistant Examiner* — Pancham Bakshi
(74) *Attorney, Agent, or Firm* — Oblon, Spivak, McClelland, Maier & Neustadt, L.L.P.

(57) ABSTRACT

Disclosed is a method for producing an alicyclic alcohol represented by general formula (III) which is useful as a starting material for a flavor mixture or the like at low cost in high yield. The alicyclic alcohol represented by general formula (III) is produced by preparing a cyclohexanecarbonyl compound represented by general formula (II) through the carbonylation of an unsaturated hydrocarbon represented by general formula (I) (preferably a compound obtained through the partial reduction of a diene compound) using carbon monoxide in the presence of HF, and thereafter reducing the cyclohexanecarbonyl compound. In formulae (I), (II), and (III), $R^1$ represents an alkyl group having 1 to 4 carbon atoms, $R^2$ represents an alkyl group having 1 to 4 carbon atoms, $R^3$ represents an OH group, fluorine, or an $OR^4$ group, and $R^4$ represents an alkyl group having 1 to 4 carbon atoms.

20 Claims, No Drawings

METHOD FOR PRODUCING ALICYCLIC ALCOHOL

TECHNICAL FIELD

The present invention relates to a method for producing an alicyclic alcohol which is useful as a starting material for a flavor mixture or the like.

BACKGROUND ART

The Patent Document 1 discloses that alicyclic alcohols represented by the following general formula (III) include one useful as a starting material for a flavor mixture. The Patent Document also discloses a method for producing the alicyclic alcohols represented by the following general formula (III), wherein, for example, 4-isopropyl-1-methylcyclohexyl methanol is produced by reducing an unsaturated alcohol produced from 1-isopropyl-4-methyl-1,3-cyclohexadiene and formaldehyde by using an acid catalyst. However, the above method has problems such that, since 1-isopropyl-4-methyl-1,3-cyclohexadiene which is the starting material in this method has a conjugated double bond, the compound is deteriorated in stability under the presence of an acid catalyst, and moreover, since it has plural reaction active sites, it has low selectivity of reaction in low yield.

In addition, 1-isopropyl-4-methyl-1,3-cyclohexadiene which is the starting material is not contained in a usual natural essential oil in a high concentration, and therefore, it is necessary to use a distillation column having a number of steps, or to isolate by distillation after increasing the content of the intended diene compounds by isomerization reaction, which causes a major problem in terms of supply and price.

[Chemical Formula 1]

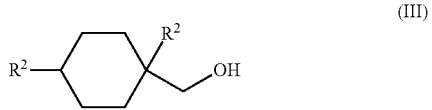

(III)

In the above formula (III), $R^1$ represents an alkyl group having 1-4 carbon atoms. $R^1$ represents an alkyl group having 1-4 carbon atoms.

The Non-patent Document 1 discloses that 4-isopropyl-1-methylcyclohexane carboxylic acid is produced by carbonylating p-menthene-1 using $BF_3$ as a catalyst, which, however, requires a carbon monoxide pressure of 100 atm or higher for the carbonylation reaction. The Non-patent Document 1 discloses that, for the purpose of identification, 4-isopropyl-1-methylcyclohexane carboxylic acid thus obtained is subjected to methyl esterification followed by reducing by $LiAlH_4$ to obtain 4-isopropyl-1-methylcyclohexyl methanol. However, it does not disclose a detailed description of the method.

When a carboxylic acid is subjected to alkyl esterification, in general, it is reacted with an alcohol in the presence of an acid catalyst by removing water. In the case of a tertiary branched carboxylic acid such as 4-isopropyl-1-methylcyclohexane carboxylic acid, however, the rate of esterification reaction is slow and the yield is low. Therefore, it is not easy to carry out alkyl esterification in an efficient manner after obtaining 4-isopropyl-1-methylcyclohexane carboxylic acid according to the method disclosed in the Non-patent Document 1. Thus, it cannot be said that it is a suitable industrial manufacturing method for obtaining an intended 4-isopropyl-1-methylcyclohexyl methanol in high yield.

Whereas the method for carbonylation of a monoene compound under the presence of HF is publicly known by the Patent Document 2, and the method for producing an alcoholic compound by hydrogenation of an carbonyl compound is publicly known by the Patent Document 3, it had not been known to combine these processes of carbonylation and hydrogenation with the process for producing an alicyclic alcohol represented by the above general formula (III) which is useful as a starting material for a flavor mixture. In addition, it had not been known to produce the above-described alicyclic alcohol easily by using, as a starting material, natural essential oils which are beneficial in terms of supply and price such as limonene that is an easily-available natural product.

PRIOR ART DOCUMENTS

Patent Document

Patent Document 1: Jpn. Pat. No. 4102412
Patent Document 2: Jpn. Pat. Laid-Open Publication No. 2006-282658
Patent Document 3: Jpn. Pat. Laid-Open Publication No. 2000-001447

Non-Patent Document

Non-patent Document 1: Izvestiya Akademii Nauk SSSR, Seriya Khimicheskaya No. 4, p 841-847(1979), (Chemical Abstract Vol. 91, No. 70749)

DISCLOSURE OF THE INVENTION

Problems to be Solved by the Invention

The problem of the present invention is to solve the above problems and to provide a method for producing an alicyclic alcohol useful as a starting material for a flavor mixture or the like at low cost in high yield.

Means for Solving the Problems

The present inventors studied a method for producing an alicyclic alcohol represented by the general formula (III) from an unsaturated hydrocarbon represented by the following general formula (I) and as a result, they found that the unsaturated hydrocarbon represented by the general formula (I) can be carbonylated in high yield in the presence of HF under a low carbon monoxide (CO) pressure of 5 MPa or lower to produce a cyclohexanecarbonyl compound in high yield, and thereafter, by reducing the cyclohexanecarbonyl compound, an intended alicyclic alcohol can be obtained in high yield.

The present invention was thus completed by the above findings.

[Chemical Formula 2]

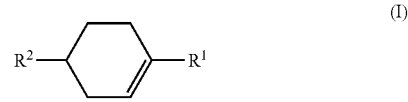

(I)

-continued

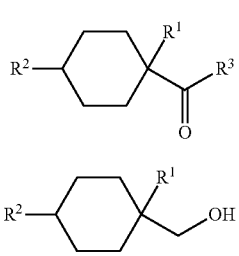

In the formulas, $R^1$ represents an alkyl group having 1-4 carbon atoms. $R^2$ represents an alkyl group having 1-4 carbon atoms. $R^3$ represents an OH group, fluorine or an OR group. $R^4$ represents an alkyl group having 1-4 carbon atoms.

That is, the present invention relates to a method for producing an alicyclic alcohol shown as follows:

[1] A method for producing an alicyclic alcohol which comprises
producing a cyclohexanecarbonyl compound represented by the general formula (II) by the carbonylation of an unsaturated hydrocarbon represented by the general formula (I) using carbon monoxide in the presence of HF, and thereafter,
producing an alicyclic alcohol represented by the general formula (III) by reducing said cyclohexanecarbonyl compound represented by the general formula (II),

[Chemical Formula 3]

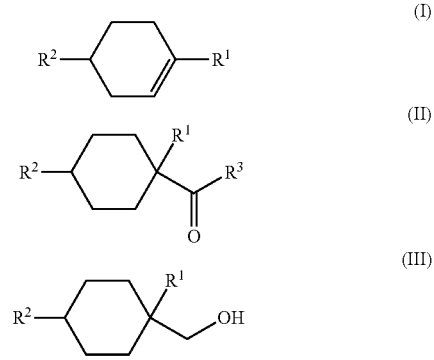

wherein $R^1$ represents an alkyl group having 1-4 carbon atoms, $R^2$ represents an alkyl group having 1-4 carbon atoms, $R^3$ represents an OH group, fluorine or an $OR^4$ group and $R^4$ represents an alkyl group having 1-4 carbon atoms.

[2] The method according to [1], wherein said carbonylation is carried out under a carbon monoxide pressure of 5 MPa or lower.

[3] The method according to [1] or [2], wherein said carbonylation is carried out at a temperature of from −50° C. to −25° C.

[4] The method according to any one of [1] to [3], wherein $R^1$ in said general formula (II) is an $OR^1$ group wherein $R^1$ represents an alkyl group having 1-4 carbon atoms.

[5] The method according to any one of [1] to [4], wherein the purity of a cis-form of said cyclohexanecarbonyl compound represented by the general formula (II) produced by the carbonylation is 85% or more.

[6] The method according to any one of [1] to [5], wherein said cyclohexanecarbonyl compound represented by the general formula (II) is reduced by using hydrogen.

[7] The method according to any one of [1] to [6], wherein said cyclohexanecarbonyl compound represented by the general formula (II) is reduced by using hydrogen and a catalyst comprising at least one selected from the metals of the 8-11 groups in the periodical table.

[8] The method according to any one of [1] to [7], wherein said unsaturated hydrocarbon represented by the general formula (I) is obtained by partial reduction of a diene compound.

[9] The method according to [8], wherein said diene compound is limonene.

[10] The method according to [8] or [9], wherein said partial reduction of a diene compound is carried out by using hydrogen and a catalyst comprising at least one selected from the metals of the 8-11 groups in the periodical table.

[11] The method according to any one of [8] to [10], wherein said partial reduction of a diene compound is carried out under a hydrogen pressure of 4 MPa or lower.

Effect of the Invention

According to the present invention, an alicyclic alcohol represented by the general formula (III) can be produced in high yield from an unsaturated hydrocarbon represented by the general formula (I) under a low CO pressure.

According to said method, in addition, the intended alicyclic alcohol can be obtained at low cost in high yield by using, as a starting material, natural products which are available without any difficulty such as limonene.

Furthermore, the method of the present invention is excellent in selectivity of a cis-form, and thus, an alicyclic alcohol having a high purity of a cis-form excellent in aromatic odor can be obtained.

MODES FOR CARRYING OUT THE INVENTION

The method of the present invention at least comprises:
(1) a process wherein a cyclohexanecarbonyl compound represented by the general formula (II) (hereinafter, "an alicyclic carbonyl compound") is produced by the carbonylation of an unsaturated hydrocarbon represented by the general formula (I) (hereinafter, "a monoene compound") using carbon monoxide in the presence of HF (=hydrogen fluoride); hereinafter, "the carbonylation process",
and
(2) a process wherein an alicyclic alcohol represented by the general formula (III) is produced by reducing said cyclohexanecarbonyl compound thus obtained; hereinafter "a carbonyl group-reduction process" or "an alicyclic alcohol-synthesis process".

<Carbonylation Process>

The carbonylation reaction of a monoene compound is carried out under a carbon monoxide pressure in the presence of HF. Thereby, a cis-form and a trans-form of an alicyclic carbonyl compound represented by the following formulas are obtained together with various by-products including other isomers.

[Chemical Formula 4]

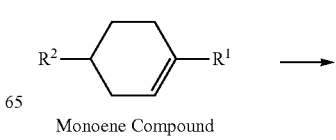

Monoene Compound

-continued

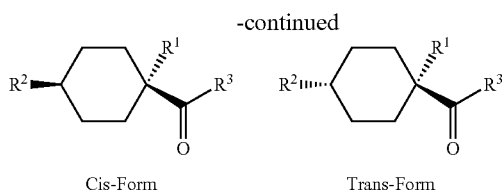

Cis-Form          Trans-Form

In the formulas, $R^1$ to $R^3$ represent same as the above.
[Monoene Compound]

In the monoene compound represented by the general formula (I), $R^1$ represents an alkyl group having 1-4 carbon atoms. $R^1$ is preferably a methyl group or an ethyl group, more preferably a methyl group, in terms of a perfume tone of the alicyclic alcohol represented by the general formula (III) obtained according to the present invention.

$R^2$ represents an alkyl group having 1-4 carbon atoms. $R^1$ is preferably an alkyl group having 2-4 carbon atoms, more preferably an isopropyl group, in terms of a perfume tone of the alicyclic alcohol represented by the general formula (III).

The monoene compound represented by the general formula (I) can be synthesized by, for example, partial hydrogenation of a corresponding diene compound using a hydrogenation catalyst.

The monoene compound thus synthesized can be used after carrying out the removal of a catalyst by filtration or the like and/or the purification by distillation or the like. However, it is usually used directly after only removing a catalyst and is brought into the carbonylation reaction without separating the solvent used in the reaction process of the monoene compound or separating a reaction by-product which is a fully hydrogenated by-product.

(Synthesis of Monoene Compound)

As a diene compound used for synthesizing a monoene compound (hereinafter, "a diene compound"), a compound which is a hydrocarbon having a six-membered ring skeleton and having hydrocarbon groups having 1-4 carbon atoms at only the 1-position and 4-position of the six-membered ring skeleton respectively. Examples thereof include alicyclic hydrocarbons and terpene hydrocarbons. Preferable examples thereof include limonene, α-terpinene, β-terpinene, γ-terpinene, isolimonene, α-phellandrene, β-phellandrene, menogene, terpinolene and dipentene. More preferable examples thereof include limonene, α-terpinene, γ-terpinene, α-phellandrene, terpinolene and dipentene. Most preferable examples thereof include limonene in terms of availability. Limonene is contained in large quantity in natural essential oils obtained by peels of oranges, lemons, grapefruits or the like, and the one with the purity of 98% can be obtained easily by steam distillation. In addition, since limonene has other uses and is industrially manufactured, it is available at low cost.

A hydrogenation catalyst of the diene compound should not be particularly limited as long as it can commonly be used for hydrogenation of an unsaturated bond. It is preferable to use a catalyst containing at least one selected from the metals of the 8-11 groups in the periodical table.

Examples of the catalysts include a catalyst containing at least one selected from the group consisting of iron, cobalt, nickel, copper, ruthenium, rhodium, palladium, silver, osmium, iridium, platinum and gold.

The hydrogenation catalyst can be a solid catalyst or a homogeneous catalyst. It is preferable to use a solid catalyst in terms of separating performance from the reaction product.

Examples of the solid catalyst include a non-carried metal catalyst and a carried metal catalyst. Examples of the non-carried metal catalyst include a Raney catalyst such as Raney nickel, Raney cobalt and Raney copper, oxides of platinum, palladium, rhodium, ruthenium or the like and a colloid catalyst.

Examples of the carried metal catalyst include a catalyst wherein at least one selected from the group consisting of iron, cobalt, nickel, copper, ruthenium, rhodium, palladium, silver, osmium, iridium, platinum and gold is carried by or mixed with a carrier such as magnesia, zirconia, ceria, diatom earth, activated charcoal, alumina, silica, zeolite and titania.

Preferable examples thereof include a carried copper catalyst such as a copper-chrome catalyst (Adkins Catalyst), a copper-zinc catalyst or a copper-iron catalyst, a carried platinum catalyst such as Pt/C and Pt/alumina, a carried palladium catalyst such as Pd/C and Pd/alumina, a carried ruthenium catalyst such as Ru/C and Ru/alumina and a carried rhodium catalyst such as Rh/C and Rh/alumina. Among them, it is more preferable to use a catalyst containing copper in terms of reaction activity and selectivity.

Though the used amount of the hydrogenation catalyst varies depending on the type of catalysts, it is proper to use in the amount of 0.001-100 mass %, preferably 0.01-30 mass %, more preferably 0.1-20 mass % based upon the amount of a diene compound as a starting material.

Hydrogenation can be carried out under ordinary pressure or under increased pressure. Normally, the hydrogen pressure is in the range of 0.1-4.0 MPa, preferably 0.1-3.0 MPa, more preferably 0.1-2.0 MPa.

The hydrogenation reaction can be carried out without using solvent or using solvent. Examples of the solvents include water, organic acids such as formic acid and acetic acid, esters such as ethyl acetate and butyl acetate, aromatic compounds such as benzene, o-dichlorobenzene, toluene and xylene, hydrocarbons such as hexane, heptane and cyclohexane, alcohols such as methanol, ethanol, isopropylalcohol, t-butylalcohol, ethyleneglycol and diethyleneglycol, ethers such as dioxane, tetrahydrofuran, dimethoxyethane and diglyme, or the mixtures thereof.

The amount of solvent in the case of using solvent for hydrogenation reaction is normally in the range of 0.1-30 mass times, preferably 0.2-20 mass times based upon the amount of the diene compound as a starting material.

The reaction temperature of hydrogen reaction is normally in the range of from −90° C. to 200° C., preferably from 20° C. to 150° C., more preferably from 20° C. to 100° C.

The reaction mode of hydrogenation reaction should not be limited as long as catalytic hydrogenation reaction can be carried out, and publicly-known reactors commonly used can be used. Examples of the reactors include a suspended-bed reactor wherein catalytic hydrogenation reaction is carried out by fluidizing the catalyst with fluid, a fixed-bed reactor wherein catalytic hydrogenation reaction is carried out by feeding a fluid by filling and fixing the catalyst, or the like.

[Carbon Monoxide]

Carbon monoxide used in the carbonylation process of the present invention can contain inert gases such as nitrogen, methane or the like. However, it is preferable to carry out under the partial pressure of carbon monoxide in the range of 0.5-5 MPa, preferably 1-3 MPa. When the partial pressure of carbon monoxide is higher than 0.5 MPa, the carbonylation reaction is made progress sufficiently and the intended alicyclic carbonyl compound can be obtained in high yield without occurring side reactions such as disproportionation and polymerization. In addition, it is preferable that the partial pressure of carbon monoxide is 5 MPa or lower in terms of an equipment load.

[Hydrogen Fluoride]

Since HF used in the carbonylation process acts as a reaction solvent, a catalyst and an auxiliary material, a substantially anhydrous one is used. The used amount of HF is 4-15 molar times, preferably 6-10 molar times based upon the amount of the monoene compound as a starting material. When the molar ratio of HF is 4 molar times or more, the carbonylation reaction is made progress efficiently, side reactions such as disproportionation and polymerization can be inhibited and the intended alicyclic carbonyl compound can be obtained in high yield. In addition, it is preferable to use HF in the amount of 15 molar times or less in terms of raw material cost and productivity.

[Reaction Conditions]

The mode of the carbonylation reaction should not particularly be limited, and any methods of batch reaction, semicontinuous reaction and continuous reaction can be employed.

The reaction temperature of the carbonylation reaction is from −50° C. to 30° C., preferably −40° C. to 0° C., most preferably −50° C. to −25° C. When the reaction temperature of the carbonylation reaction is 30° C. or lower, especially −25° C. or lower, selectivity of a cis-form is favorable. In addition, it is preferable to carry out the reaction at −50° C. or higher in terms of the rate of reaction.

The selectivity of a cis-form means the ratio of a cis-form of the alicyclic carbonyl compound in the carbonylated products. When this value is higher, the yield in the purification process becomes better and a high-quality alicyclic carbonyl compound can be obtained. According to the preferable method of the present invention, an alicyclic carbonyl compound having the 85% or higher purity of a cis-form can be obtained. The purity of a cis-form of the alicyclic carbonyl compound means the ratio of a cis-form of the alicyclic carbonyl compound based upon the total amount of carbonylated product including all by-products such as other isomers.

In the carbonylation reaction, an acid fluoride which is a compound represented by (II) wherein $R^3$ is fluorine is produced by HF and carbon monoxide. The reaction mixture of an acid fluoride thus obtained is purified in the usual manner such as distillation after removing excessive HF. Then it can be used as a starting material in the next alicyclic alcohol-synthesis process. However, it is common to employ a method of reacting with water to produce an alicyclic carboxylic acid represented by the general formula (II) wherein $R^3$=OH or a method of reacting with an alcohol represented by the general formula (IV):

$$R^1\text{—OH} \tag{IV}$$

wherein $R^4$ represents an alkyl group having 1-4 carbon atoms, hereinafter, "alcohol (IV)", to produce an alicyclic ester compound represented by the general formula (II) wherein $R^3$=$OR^4$. It is preferable to convert to an alicyclic ester compound in terms of an equipment load. That is, as a compound represented by the general formula (II) in the present invention, an ester compound is more suitable than a carboxylic acid or an acid fluoride.

(Convert to Alicyclic Carboxylic Acid or Alicyclic Ester Compounds)

In the case of synthesizing an alicyclic carboxylic acid or an alicyclic ester compound by reacting the reaction mixture produced by the carbonylation reaction with water or the alcohol (IV), it is possible to isolate an acid fluoride once and then to react again with water or the alcohol (IV) in the presence of HF catalyst. However, it is common to employ a method of reacting with water or the alcohol (IV) directly without isolating an acid fluoride to produce an alicyclic carboxylic acid. In this case, it is preferable to add a predetermined amount of water or the alcohol (IV) to the acid fluoride reaction mixture in terms of corrosiveness of the reaction apparatus.

With regard to the alcohol represented by the general formula (IV), $R^4$ represents an alkyl group having 1-4 carbon atoms. Examples of the alcohol include methanol, ethanol, n-propanol, i-propanol, n-butylalcohol, i-butylalcohol and t-butylalcohol. Among them, methanol or ethanol is preferable in terms of reactivity.

The amount to be used of the alcohol is 0.5-2.0 molar times, preferably 0.8-1.5 molar times based upon the amount of the monoene compound as a starting material of the carbonylation process. The molar ratio of the alcohol (IV) of 0.5 molar times or more is preferable for the reason that the remaining amount of unreacted fluoride is small and corrosion of the apparatus of the following process is inhibited. The molar ratio of the alcohol (IV) of 2.0 molar times or less is preferable in terms of corrosion-inhibition effect of the apparatus by inhibiting the intermolecular dehydration reaction of alcohol.

The reaction temperature of the reaction between the acid fluoride and water or the alcohol (IV) is preferably 20° C. or lower in terms of inhibiting decomposition of an alicyclic carboxylic acid or an alicyclic ester compound. In the case of reaction with the alcohol (IV), especially, the reaction temperature of 20° C. or lower is preferable for the reason that the intermolecular dehydration reaction of alcohol can be inhibited.

After distilling HF away from the alicyclic carboxylic acid or the alicyclic ester compound thus obtained, purification is carried out in the usual manner such as distillation and thus an alicyclic carboxylic acid or an alicyclic ester compound having high selectivity of a cis-form can be obtained.

<Carbonyl Group-Reduction Process>

In the carbonyl group-reduction process, a cis-form and a trans-form of the cyclohexanecarbonyl compound represented by the general formula (II) obtained by the carbonylation process are reduced to produce a corresponding cis-form and trans-form of a cyclic alcohol respectively.

[Chemical Formula 5]

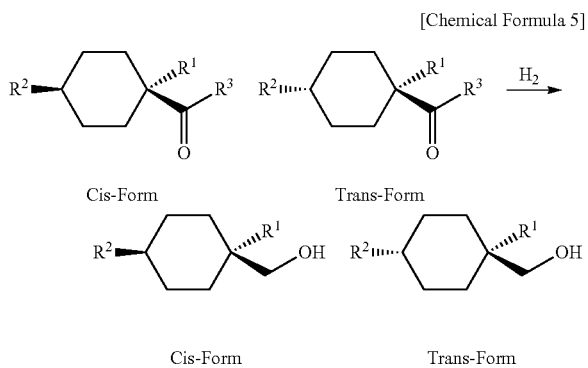

In the formula, $R^1$-$R^3$ represent same as above.

Methods for reducing the cyclohexanecarbonyl compound represented by the general formula (II) obtained by the carbonylation process are not particularly limited, and any methods commonly employed for reducing a carbonyl compound to an alcohol can be used. For example, any methods such as hydride reduction disclosed in The Fifth Series of Experimental Chemistry, Vol. 14, p 11-27, Maruzen, reduction by metal or metal salts and catalytic hydrogenation can be used. Reduction by catalytic hydrogenation is preferable in terms of the economic efficiency.

Catalysts to be used for catalytic hydrogenation of a cyclohexanecarbonyl compound should not particularly be limited as long as they are commonly used for hydrogenation of carbonyl compounds. It is preferable to use a catalyst containing at least one selected from the metals of the 8-11 groups in the periodical table.

Examples of the catalysts include a catalytic hydrogenation catalyst containing at least one selected from the group consisting of iron, cobalt, nickel, copper, ruthenium, rhodium, palladium, silver, osmium, iridium, platinum and gold.

The catalytic hydrogenation catalyst can be a solid catalyst or a homogeneous catalyst. It is preferable to use a solid catalyst in terms of separating performance from the reaction product. Examples of the solid catalyst include a non-carried metal catalyst and a carried metal catalyst.

Examples of the non-carried metal catalyst include a Raney catalyst such as Raney nickel, Raney cobalt and Raney copper, oxides of platinum, palladium, rhodium, ruthenium or the like and a colloid catalyst.

Examples of the carried metal catalyst include a catalyst wherein at least one selected from the group consisting of iron, cobalt, nickel, copper, ruthenium, rhodium, palladium, silver, osmium, iridium, platinum and gold is carried by or mixed with a carrier such as magnesia, zirconia, ceria, diatom earth, activated charcoal, alumina, silica, zeolite and titania.

Preferable examples thereof include a carried copper catalyst such as a copper-chrome catalyst (Adkins Catalyst), a copper-zinc catalyst or a copper-iron catalyst, a carried platinum catalyst such as Pt/C and Pt/alumina, a carried palladium catalyst such as Pd/C and Pd/alumina, a carried ruthenium catalyst such as Ru/C and Ru/alumina, a carried rhodium catalyst such as Rh/C and Rh/alumina and a carried nickel catalyst such as nickel/alumina (=a Raney nickel catalyst), nickel/diatom earth (=a stabilized nickel catalyst) and nickel/zirconia.

Among them, it is more preferable to use a catalyst containing nickel and/or copper in terms of reaction activity.

Though the used amount of the catalytic hydrogenation catalyst varies depending on the type of catalysts, it is proper to use in the amount of 1-100 mass %, preferably 3-30 mass % based upon the amount of a cyclohexanecarbonyl compound as a starting material.

[Solvent]

The carbonyl group-reduction process of the present invention can be carried out without using solvent or using solvent.

Examples of the solvents for the carbonyl group-reduction process of the present invention include water, organic acids such as formic acid and acetic acid, esters such as ethyl acetate and butyl acetate, aromatic compounds such as benzene, o-dichlorobenzene, toluene and xylene, hydrocarbons such as hexane, heptane and cyclohexane, alcohols such as methanol, ethanol, isopropylalcohol, t-butylalcohol, ethyleneglycol and diethyleneglycol, ethers such as dioxane, tetrahydrofuran, dimethoxyethane and diglyme, or the mixtures thereof.

Among them, it is preferable to use no solvent or to use aromatic compounds such as benzene, o-dichlorobenzene, toluene and xylene, hydrocarbons such as hexane, heptane and cyclohexane, alcohols such as methanol, ethanol, isopropylalcohol, t-butylalcohol, ethyleneglycol and diethyleneglycol, ethers such as dioxane, tetrahydrofuran, dimethoxyethane and diglyme, or the mixtures thereof.

The amount of solvent in the case of using a solvent in the carbonyl group-reduction process of the present invention is normally in the range of 0-30 mass times, preferably 0-20 mass times based upon the amount of the cyclohexanecarbonyl compound represented by the general formula (II) obtained by the carbonylation process.

[Reaction Conditions]

Regarding the hydrogen pressure in the carbonyl group-reduction process of the present invention, a higher pressure is preferable in terms of shifting the reaction equilibrium to the side of alcohol. Concerning the equipment cost, however, the preferable hydrogen pressure is 1-30 MPa, more preferably 2-20 MPa, most preferably 5-10 MPa.

The reaction temperature in the carbonyl group-reduction process of the present invention is preferably 100° C. or higher, more preferably 150° C. or higher in terms of ensuring a sufficient reaction rate. In addition, it is preferably 300° C. or lower, more preferably 280° C. or lower, most preferably 250° C. or lower in terms of inhibiting the ester exchange reaction between the alicyclic alcohol thus produced and the intermediate ester compounds The mode of the carbonyl group-reduction process of the present invention should not particularly be limited. In the case of carrying out the process by catalytic hydrogenation, the mode should not particularly be limited as long as catalytic hydrogenation reaction can be carried out, and publicly known methods which are commonly used can be employed. Examples of the reactors include a suspended-bed reactor wherein catalytic hydrogenation reaction is carried out by fluidizing the catalyst with fluid, a fixed-bed reactor wherein catalytic hydrogenation reaction is carried out by feeding a fluid by filling and fixing the catalyst, or the like.

In the case of using an alicyclic carboxylic acid or an alicyclic ester compound as the cyclohexanecarbonyl compound which is the starting material, water or alcohols having 1-4 carbon atoms are produced as a by-product. The reaction can be carried out under the presence of these by-products or can be carried out by removing them continuously or intermittently during the reaction.

After separating the hydrogenation catalyst off from the alicyclic alcohol product thus obtained, purification is carried out according in the usual manner such as distillation, and thus a high-purity alicyclic alcohol having the high content of a cis-form, preferably an alicyclic alcohol having the 85% or higher purity of a cis-form can be obtained.

The purity of a cis-form here means the ratio of a cis-form of the alicyclic alcohol based upon the total amount of the alicyclic alcohol product including all the by-products such as other isomers.

EXAMPLES

The present invention will be described in more detail below referring to Examples, which are not intended to limit the scope of the present invention.

In the description below, if not otherwise specified, means "mass %".

<Conditions of Gas Chromatographic Analysis>

In the case of analyzing a monoene compound and an alicyclic alcohol, the trade name "GC-17A", manufactured by Shimadzu Corporation, was used as a gas chromatography and the trade name "HR-1", 0.32 mmφ×25 m, manufactured by Shinwa Chemical Industries, Ltd., was used as a capillary column. The temperature was raised from 100° C. to 250° C. at the rate of 2° C./min.

In the case of analyzing a cyclohexanecarbonyl compound, the trade name "GC-17A", manufactured by Shimadzu Corporation, was used as a gas chromatography and the trade name "DBWAX", 0.32 mmφ×30 m, manufactured by J&W, was used as a capillary column. The temperature was raised from 100° C. to 250° C. at the rate of 5° C./min.

Example of Preparation 1

Preparation of 4-isopropyl-1-methylcyclohexene, Hereinafter, "DH-Terpinene", by Hydrogenation of Limonene

[Chemical Formula 6]

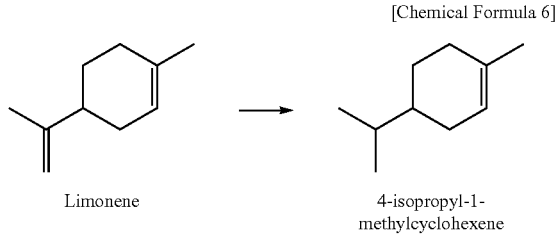

Limonene      4-isopropyl-1-methylcyclohexene 50.0 g of a Cu—Cr catalyst, trade name "N-203S", manufactured by JGC Catalyst and Chemicals Ltd., and 500.0 g of heptane, a special grade, manufactured by Wako Pure Chemical Industries Ltd., were charged into a stainless-steel autoclave having the internal volume of 5 L equipped with a Nac drive stirrer, three entry nozzles on the top and one extract nozzle at the bottom capable of controlling the internal temperature by a jacket, and activation was carried out for 1 hour.

After cooling, 500.0 g of limonene, manufactured by YASUHARA CHEMICAL CO., LTD., was charged and hydrogenation reaction was carried out by stirring for 3 hours at 95° C. under the hydrogen pressure of 2 MPa. The reaction mixture was then filtrated to remove catalyst to obtain 957.4 g of the reaction mixture containing 4-isopropyl-1-methylcyclohexene in a concentration of 49.0%, 4-isopropyl-1-methylcyclohexane in a concentration of 1.4% and heptane in a concentration of 49.6%. The yield was 92.5%.

Example 1

Production of Ethyl 4-isopropyl-1-methylcyclohexanoate, Hereinafter, "DHT-Ester", by Carbonylation and Esterification of DH-Terpinene

[Chemical Formula 7]

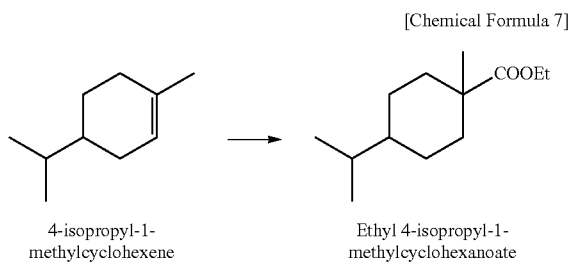

4-isopropyl-1-methylcyclohexene      Ethyl 4-isopropyl-1-methylcyclohexanoate

<Carbonylation Process>

The experiment was carried out by using a stainless-steel autoclave having the internal volume of 500 ml equipped with a Nac drive stirrer, three entry nozzles on the top and one extract nozzle at the bottom capable of controlling the internal temperature by a jacket.

Firstly, the inner air of the autoclave was replaced by carbon monoxide, and subsequently, 100 g of hydrogen fluoride was introduced therein. After adjusting the liquid temperature at −30° C., carbon monoxide pressure was applied up to 2 MPa.

Keeping the reaction temperature at −30° C. and the reaction pressure at 2 MPa, 201.3 g of the reaction mixture prepared in the Example of Preparation 1 containing 4-isopropyl-1-methylcyclohexene in a concentration of 49.0%, 4-isopropyl-1-methylcyclohexane in a concentration of 1.4% and heptane in a concentration of 49.6%, wherein the content of 4-isopropyl-1-methylcyclohexene was 0.71 mol, was fed into the autoclave from its top to carry out the carbonylation reaction.

After completion of feeding, stirring was continued for approximately 10 minutes until the absorption of carbon monoxide was not detected.

<Esterification>

Subsequently, keeping the reaction temperature at −30° C., 49.3 g (1.07 mol) of ethanol was fed into the autoclave from its top, and esterification was carried out by stirring for 1 hour.

The reaction mixture was extracted from the bottom of the autoclave into ice water. After separating the oil phase from the aqueous phase, the oil phase was washed with 100 ml of 2%-sodium hydroxide aqueous solution for two times and 100 ml of distilled water for two times, and then dehydrated by 10 g of anhydrous sodium sulfate. As a result of analyzing the liquid mixture thus obtained by gas chromatography, it was found that the reaction mixture contains the following two types of the alicyclic ester compound.

[Chemical Formula 8]

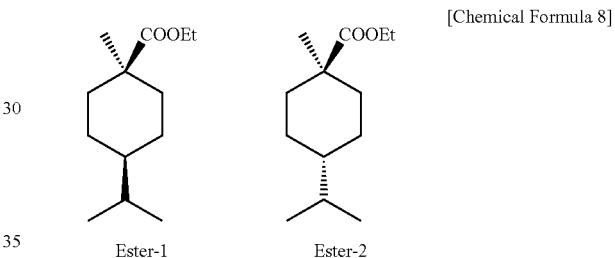

Ester-1      Ester-2

Regarding the proportion of each alicyclic ester compound in the mixture of the two alicyclic ester compounds, ethyl cis-4-isopropyl-1-methylcyclohexanoate (=Ester-1) was 89.8%, ethyl trans-4-isopropyl-1-methylcyclohexanoate (=Ester-2) was 3.8% and other isomers were 6.4%.

The liquid mixture thus obtained was further subjected to removal of low-boiling components by an evaporator, and then to purification using a rectifier having the number of theoretical stages of 20 stages at the distillation temperature of 150° C. under the degree of vacuum of 60 torr. As a result, 142.4 g of an ester mixture containing 89.4% of Ester-1 and 3.6% of Ester-2 was obtained as a main fraction of distillate, wherein the total yield of Ester-1 and Ester-2 was 87.4 mol % based upon the amount of 4-isopropyl-1-methylcyclohexene.

Production of DHT-Alcohol {=(4-isopropyl-1-methylcyclohexyl)methanol} by Reducing DHT-Ester; Carbonyl Group-Reduction Process

[Chemical Formula 9]

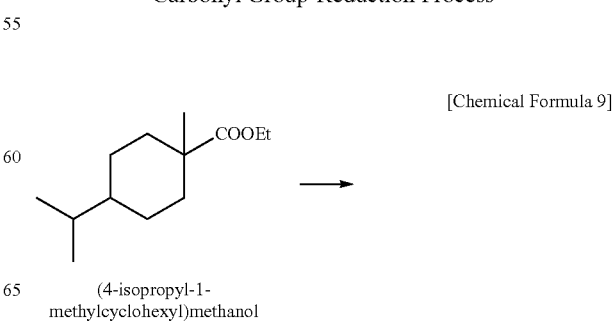

(4-isopropyl-1-methylcyclohexyl)methanol

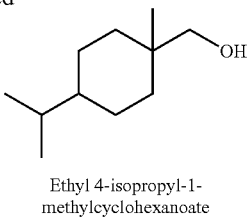

Ethyl 4-isopropyl-1-methylcyclohexanoate 5.3 g of a copper-zinc catalyst carried by alumina, manufactured by JGC Catalysts and Chemicals Ltd., and 105 g of the ester mixture obtained as a maim fraction of distillate as above which contains 89.4% of ethyl cis-4-isopropyl-1-methylcyclohexanoate and 3.6% of ethyl trans-4-isopropyl-1-methylcyclohexanoate were charged into the stainless-steel autoclave and reduction reaction was carried out by stirring for 14 hours at 250° C. under the hydrogen pressure of 10 MPa while passing hydrogen.

After removing the catalyst from the reaction mixture by filtration, 68 g of the final product of mixture containing 85.8% of (cis-4-isopropyl-1-methylcyclohexyl)methanol (=Alcohol-1) and 3.5% of (trans-4-isopropyl-1-methylcyclohexyl)methanol (=Alcohol-2) was produced. The total yield of Alcohol-1 and Alcohol-2 was 77 mol % based upon the total amount of Ester-1 and Ester-2.

[Chemical Formula 10]

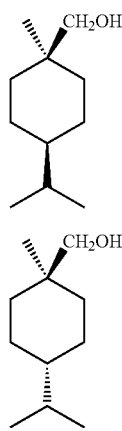

Alcohol-1

Alcohol-2

Example 2

Carbonylation Process

The experiment was carried out in the same manner as Example 1 except for using 34.3 g (1.07 mol) of methanol as an alcohol used for esterification.

As a result of analyzing the reaction mixture of esterification with methanol, the proportion of each alicyclic ester compound in the mixture of the two alicyclic ester compounds was found that methyl cis-4-isopropyl-1-methylcyclohexanoate was 89.85, methyl trans-4-isopropyl-1-methylcyclohexanoate was 3.8% and other isomers were 6.4%.

The mixture was further subjected to purification using a rectifier having the number of theoretical stages of 20 stages at the distillation temperature of 140° C. under the degree of vacuum of 60 torr. As a result, 134.5 g of an ester mixture containing 89.4% of methyl cis-4-isopropyl-1-methylcyclohexanoate and 3.6% of methyl trans-4-isopropyl-1-methylcyclohexanoate was obtained as a main fraction of distillate, wherein the total ester yield of the cis-form and the trans-form was 88.4 mol % based upon the amount of 4-isopropyl-1-methylcyclohexene.

<Carbonyl Group-Reduction Process>

The experiment was carried out in the same manner as Example 1 except for using 6.3 g of a copper-zinc catalyst carried by alumina and 125 g of the ester mixture as a starting material which contains 89.4% of methyl cis-4-isopropyl-1-methylcyclohexanoate and 3.6% of methyl trans-4-isopropyl-1-methylcyclohexanoate and changing the reaction time to 8 hours. 91 g of the final product of mixture containing 86.2% of (cis-4-isopropyl-1-methylcyclohexyl)methanol and 3.5% of (trans-4-isopropyl-1-methylcyclohexyl)methanol was produced. The total yield of Alcohol-1 and Alcohol-2 was 81 mol %; based upon the total amount of cis-4-isopropyl-1-methylcyclohexanoate and methyl trans-4-isopropyl-1-methylcyclohexanoate.

INDUSTRIAL APPLICABILITY

According to the method of the present invention, an alicyclic alcohol which is useful as a starting material for a flavor mixture or the like can be produced at low cost in high yield. In addition, since the production process can be carried out at low carbon monoxide pressure, the method is beneficial in terms of an equipment load. Furthermore, according to the method of the present invention, the selectivity of a cis-form is high and thus, an alicyclic alcohol having the high purity of a cis-form excellent in aromatic odor can be obtained.

The invention claimed is:

1. A method for producing an alicyclic alcohol, comprising:
    carbonylating an unsaturated hydrocarbon of formula (I) with carbon monoxide in the presence of HF to obtain a cyclohexanecarbonyl compound of formula (II), and then
    reducing the cyclohexanecarbonyl compound of formula (II) to obtain an alicyclic alcohol of formula (III),
    wherein formula (I), formula (II), and formula (III), respectively, are:

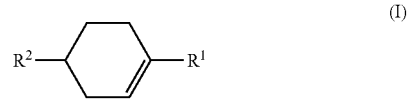

(I)

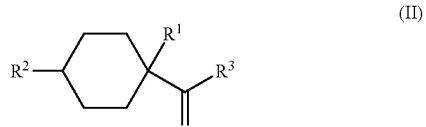

(II)

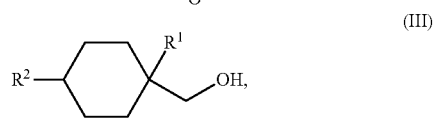

(III)

$R^1$ is an alkyl group comprising 1-4 carbon atoms,
$R^2$ is an alkyl group comprising 1-4 carbon atoms,
$R^3$ is an OH group, fluorine, or an $OR^4$ group, and
$R^4$ is an alkyl group comprising 1-4 carbon atoms.

2. The method of claim 1, wherein a carbon monoxide pressure of carbonylating the unsaturated hydrocarbon is 5 MPa or lower.

3. The method of claim 1, wherein a temperature of carbonylating the unsaturated hydrocarbon is from −50° C. to −25° C.

4. The method of claim 1,
wherein $R^3$ is an $OR^4$ group.

5. The method of claim 1, wherein carbonylating the unsaturated hydrocarbon yields a product with a content of a cis-form of the cyclohexanecarbonyl compound of formula (II) that is 85% or more.

6. The method of claim 1, wherein reducing the cyclohexanecarbonyl compound comprises reducing with hydrogen.

7. The method of claim 1, wherein reducing the cyclohexanecarbonyl compound comprises reducing with hydrogen and a catalyst comprising a metal of groups 8-11 of the periodic table.

8. The method of claim 1, wherein the unsaturated hydrocarbon of formula (I) is obtained by partially reducing a diene.

9. The method of claim 8, wherein the diene is limonene.

10. The method of claim 8,
wherein partially reducing the diene comprises partially reducing with hydrogen and a catalyst comprising a metal of groups 8-11 of the periodic table.

11. The method of claim 8, wherein a hydrogen pressure of partially reducing the diene is 4 MPa or lower.

12. The method of claim 1, wherein $R^1$ is a methyl group or an ethyl group.

13. The method of claim 10, wherein the catalyst comprises at least one non-carried metal catalyst selected from the group consisting of Raney nickel, Raney cobalt, Raney copper, a platinum oxide, a palladium oxide, a rhodium oxide, a ruthenium oxide, and a colloid catalyst.

14. The method of claim 10, wherein the catalyst comprises at least one carried metal catalyst comprising iron, cobalt, nickel, copper, ruthenium, rhodium, palladium, silver, osmium, iridium, platinum, gold, or a combination thereof, which is carried by or mixed with a carrier.

15. The method of claim 11, wherein the hydrogen pressure of partially reducing the diene is from 0.1 to 3.0 MPa.

16. The method of claim 2, wherein a carbon monoxide pressure of carbonylating the unsaturated hydrocarbon is from 1 to 3 MPa.

17. The method of claim 1, wherein a molar amount of the HF is from 4 to 15 times greater than a molar amount of the unsaturated hydrocarbon of formula (I).

18. The method of claim 7, wherein the catalyst comprises at least one non-carried metal catalyst selected from the group consisting of Raney nickel, Raney cobalt, Raney copper, a platinum oxide, a palladium oxide, a rhodium oxide, a ruthenium oxide, and a colloid catalyst.

19. The method of claim 7, wherein the catalyst comprises at least one carried metal catalyst comprising iron, cobalt, nickel, copper, ruthenium, rhodium, palladium, silver, osmium, iridium, platinum, gold, or a combination thereof, which is carried by or mixed with a carrier.

20. The method of claim 7, wherein the catalyst comprises nickel, copper, or both.

* * * * *